United States Patent
Kastendieck et al.

(10) Patent No.: US 6,634,209 B1
(45) Date of Patent: Oct. 21, 2003

(54) WEAPON FIRE SIMULATION SYSTEM AND METHOD

(75) Inventors: William A. Kastendieck, Wylie, TX (US); Terry A. Breese, Plano, TX (US); James F. Hollingsworth, Carrollton, TX (US)

(73) Assignee: Raytheon Company, Lexington, MA (US)

( * ) Notice: Subject to any disclaimer, the term of this patent is extended or adjusted under 35 U.S.C. 154(b) by 13 days.

(21) Appl. No.: 09/821,612

(22) Filed: Mar. 29, 2001

(51) Int. Cl.[7] .................................................. G01N 3/08
(52) U.S. Cl. ....................................................... 73/12.07
(58) Field of Search ............................ 73/12.01, 12.04, 73/12.05, 12.07, 12.08, 12.09

(56) References Cited

U.S. PATENT DOCUMENTS

| | | | |
|---|---|---|---|
| 3,693,432 A | * 9/1972 | Stewart et al. ............. | 73/12.05 |
| 4,480,999 A | * 11/1984 | Witherell et al. ............. | 434/18 |
| 4,862,746 A | * 9/1989 | Komatsu .................... | 73/12.12 |
| 5,277,584 A | * 1/1994 | DeGroat et al. ............... | 434/29 |
| 5,412,991 A | * 5/1995 | Hobbs .......................... | 73/663 |

* cited by examiner

Primary Examiner—Max Noori
(74) Attorney, Agent, or Firm—Baker Botts L.L.P.

(57) ABSTRACT

A method and system for simulating weapon fire includes a fixture having first and second faces. A mounting plate adapted to receive a component for testing of the component may be coupled with the first face. In a particular embodiment, a first pneumatic hammer may be coupled with the second face, the pneumatic hammer being operable to subject the component to shock pulses. A second pneumatic hammer may be coupled with the second face. The first and second pneumatic hammers may be configured to subject the component to at least two shock pulses simultaneously.

19 Claims, 5 Drawing Sheets

WEAPON FIRE SIMULATION SYSTEM AND METHOD

TECHNICAL FIELD OF THE INVENTION

The present invention relates generally to testing and evaluation of weapon components and more particularly, to a weapon fire simulation system and method.

BACKGROUND OF THE INVENTION

The increasing complexity of weapons, weapon systems and their related components has lead to increased failure of intricate, sensitive components. Accordingly, manufacturers of such components, test and evaluate each element for longevity, durability and compliance to specification. Components include thermal weapon sights, thermal sensors, detectors, coolers and various electronic components.

In order to test such components, live automatic rifle firings are typically required to provide production screening. During live testing and evaluation, the components are excited to field use shock levels. Afterwards, the weapons and weapon systems are evaluated and/or disassembled for further investigation.

SUMMARY OF THE INVENTION

The present invention provides a system and method for simulating weapon fire upon a component. A pair of pneumatic hammers may be coupled with a fixture and used to simultaneously generate shock pulses upon the component along three mutually perpendicular axes. Accordingly, the time, expense, and safety hazards associated with live weapon testing is reduced or eliminated.

In a particular embodiment, a system for simulating weapon fire includes a fixture having first and second faces. A mounting plate may be coupled with the first face. The mounting plate may be adapted to receive a component for testing of the component. In accordance with a particular embodiment, a pneumatic hammer may be coupled with the second face, and the pneumatic hammer may be operable to subject the mounting plate to shock pulses.

In accordance with another aspect of the present invention, a second pneumatic hammer may be coupled with the second face. The first pneumatic hammer may be generally positioned along a first axis and the second pneumatic hammer may be generally positioned along a second axis, wherein the first axis is generally perpendicular to the second axis.

In accordance with yet another aspect of the present invention, the pneumatic hammers may be operable to subject the component to first shock pulses along first, second and third mutually perpendicular axes. The first shock pulses may be approximately equal to second shock pulses generated during operation of an automatic weapon, along the first, second and third axis.

In accordance with still another embodiment of the present invention, the first and second pneumatic hammers may be coupled with a programmable logic controller. The programmable logic controller may be programmed to simulate weapon fire shock pulses along three mutually perpendicular axes, for predetermined time intervals.

Technical advantages of particular embodiments of the present invention include a system and method for duplicating the repetitive shock pulse train as produced by full automatic weapon firings simultaneously, along three mutually perpendicular axes. Accordingly, the system produces a Shock Response Spectrum (SRS) comparable to the SRS of a weapon, along three mutually perpendicular axes, while eliminating or reducing hazards, delays, and expense of live weapon firings.

BRIEF DESCRIPTION OF THE DRAWINGS

For a more complete understanding of the present invention and its advantages, reference is now made to the following description, taken in conjunction with the accompanying drawings, in which.

DETAILED DESCRIPTION OF THE INVENTION

Figure 1:
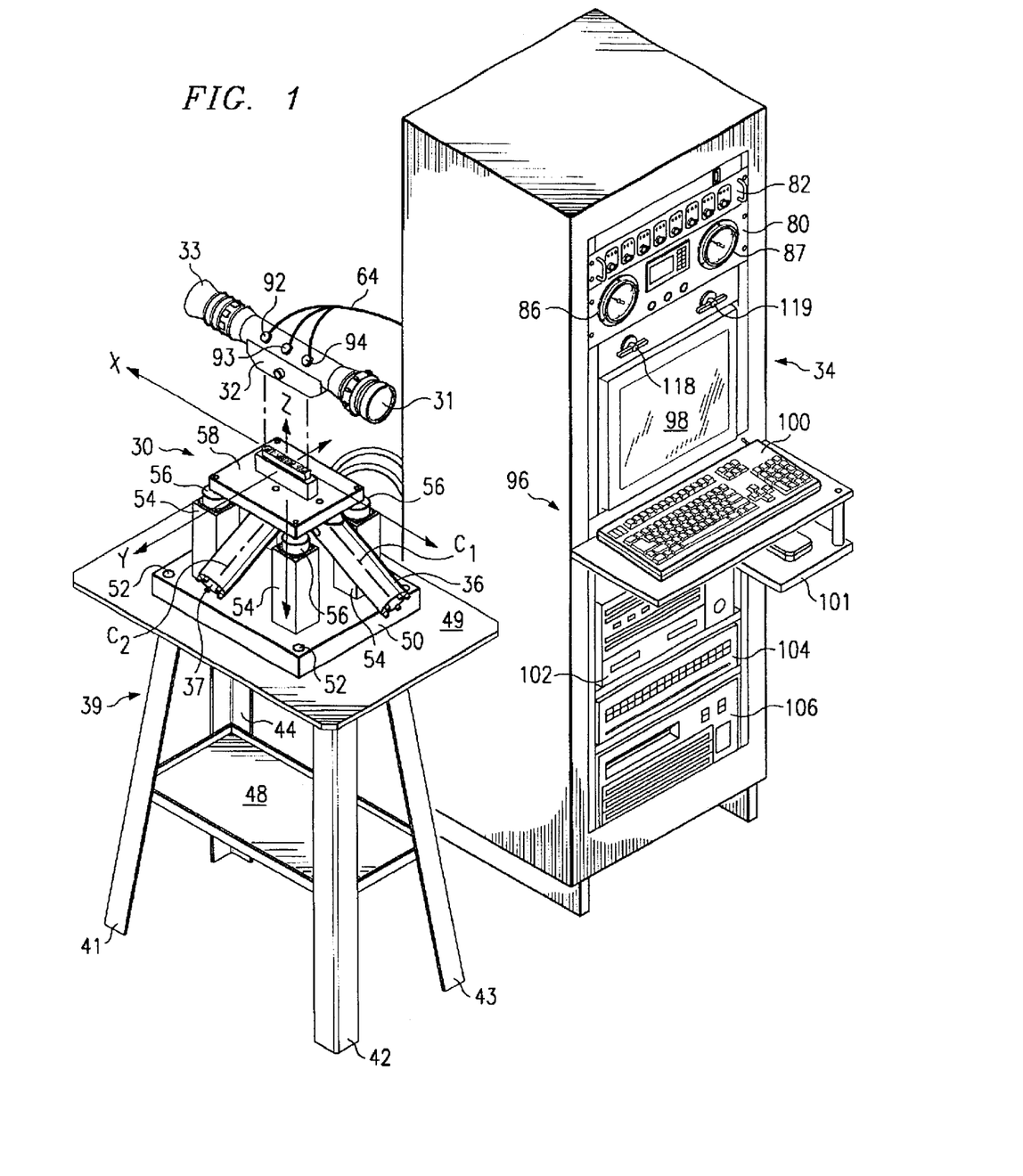
FIG. 1 is an isometric drawing illustrating a system for simulating weapon fire upon a component, in accordance with a particular embodiment of the present invention.
Figure 2:
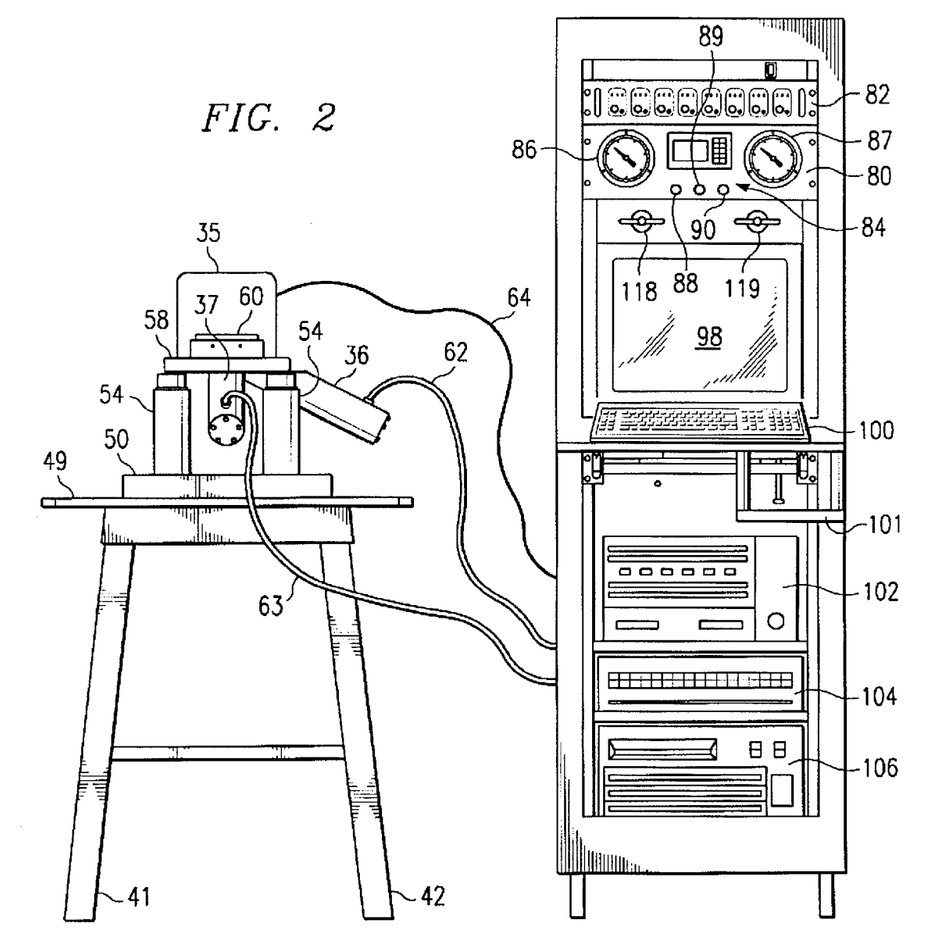
FIG. 2 is a front view illustrating the system of FIG. 1, in accordance with a particular embodiment of the present invention.

FIGS. 1 and 2 illustrate a weapon fire simulator 30 coupled with a thermal weapon site 32 and a control cabinet 34. Weapon fire simulator 30 includes two pneumatic hammers 36, 37, which subject thermal weapon site 32 to shock pulses similar to those experienced by thermal weapon site 32 during weapon firing. Accordingly, weapon fire simulator 30 provides a system and method for simulating the effect of weapon fire on thermal weapon site 32, for testing and evaluation purposes.

Under normal operating conditions, thermal weapon site 32 is coupled with a weapon or weapon system. Each round fired from the weapon produces three distinctive shock pulses which act upon thermal weapon site 32. The first shock pulse is generated by burning of the propellant. The second shock pulse is due to the recoiled gasses opening the bolt action, and the third pulse is the bolt reseating and locking into position for the next round to be fired.

During testing and evaluation, thermal weapon site 32 is coupled with weapon fire simulator 30. Simulated firing uses pneumatic hammers 36 and 37 which simultaneously generate shock pulses along three mutually perpendicular axes which mimic the shock pulses generated by a weapon, during operation. In accordance with a particular embodiment, the teachings of the present invention provide a system and method to simulate weapon firing while reducing both safety risks and costs associated with testing and evaluation of thermal weapon site 32 upon an actual weapon or weapon system.

In the illustrated embodiment of FIG. 1, weapon fire simulator 30 is mounted upon a work table 39. Work table 39 provides stability during testing. Four legs 41–44, associated with work table 39 contact a level surface during operation. A mid-shelf 48 couples each of legs 41–44, and provides additional stability to work table 39. It will be recognized by those of ordinary skill in the art that the weapon fire simulator 30 may be mounted upon any sturdy surface during operation.

Figure 3:
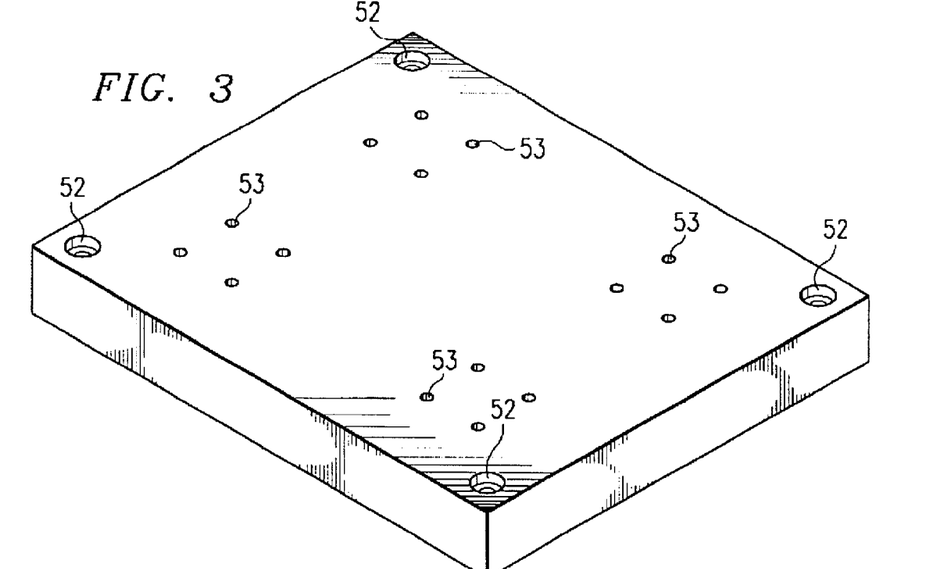
FIG. 3 is an isometric drawing illustrating a base plate of the system of FIG. 1, in accordance with a particular embodiment of the present invention.

Weapon fire simulator 30 includes a base plate 50, having a plurality of fastener openings 52. Base plate 50 is illustrated in more detail in FIG. 3. Fastener openings 52 allow base plate 50 to be secured to the top surface 49 of work table 39. Base plate 50 of the illustrated embodiment comprises a 2'×2'×3" aluminum base plate which provides seismic mass, although other materials and configurations are suitable for use within the teachings of the present invention.

Four pedestals 54 extend from, and are generally perpendicular to, surface 49 of base plate 50. In the illustrated embodiment, each pedestal 54 comprises a solid 3"×3"×8" aluminum post. Each of pedestals 54 are coupled with base plate 50. Pedestals 54 are coupled with base plate 50 using a plurality of fasteners through openings 53 (FIG. 3) and base plate 50. Each pedestal 54 includes a plurality of corresponding threaded openings which allow for threaded fasteners to be installed through base plate 50. Each pedestals 54 is coupled with a vibration isolator 56, at an end opposite base plate 50.

Each vibration isolator 56 provides a resilient support for a fixture 58. Vibration isolators 56 reduce the amount of vibration generated from fixture 58 through pedestal 54 and base plate 50, during operation. In the illustrated embodiment, vibration isolators 56 include Barry shock mounts. However, other suitable vibration isolators are available for use within the teachings of the present invention.

Figures 4, 5:
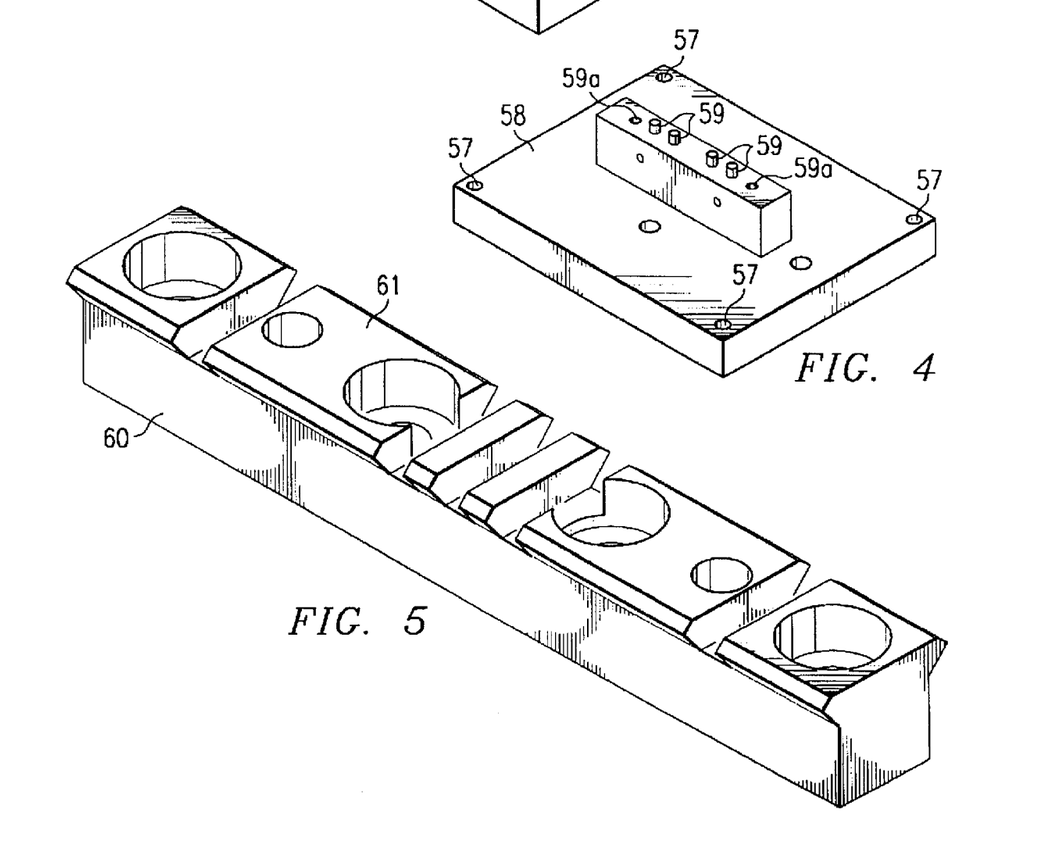
FIG. 4 is an isometric drawing illustrating a fixture of the system of FIG. 1, in accordance with a particular embodiment of the present invention.
FIG. 5 is an isometric drawing illustrating a mounting plate adapted to be coupled with the fixture of FIG. 4, in accordance with a particular embodiment of the present invention.

FIG. 4 is an isometric illustration of fixture 58. A plurality of fastener openings 57 are used to couple fixture 58 with vibration isolators 56 and pedestals 54. Fixture 58 also includes a plurality of protrusions 59 and threaded openings 59a, which are adapted to receive fasteners operable to couple a mounting plate 60, thereto.

FIG. 5 is an isometric illustration of mounting plate 60. Mounting plate 60 is coupled with fixture 58 and disposed at a central portion thereof. In the illustrated embodiment, mounting plate 60 is a 7"×10"×1" aluminum plate, and includes an upper portion 61, configured to simulate the rail of a weapon, in order to accommodate the coupling of thermal weapon site 32 with weapon fire simulator 30. For example, weapon fire simulator 30 may be configured to simulate an M16A2 rifle. In this case, the upper portion 61 of mounting plate 58 is configured similar or identical to the rail of the M16A2 rifle. Therefore, upper portion 61 of mounting plate 60 conforms to a standard MIL-STD-1913 (AR) rail, which corresponds to the M16A2. Using this configuration, thermal weapon site 32 may be coupled with weapon simulator 30 in the same manner it would be coupled with a weapon for its intended use. Furthermore, the configuration of mounting plates 60 allows weapon fire simulator 30 to subject thermal weapon site 32 to shock pulses which are similar or identical to the shock pulses exerted upon thermal weapon site 32 by various weapons and weapon systems.

In alternative embodiments, mounting plate 60 may be configured to receive practically any component for which repetitive shock pulse testing is appropriate. In the illustrated embodiment, mounting plate 60 is configured to receive any weapon sight suitable for mounting upon an M16A2 rifle. Mounting plate 60 may also be configured to simulate any M16, M2, M4, M60, M240, etc., within the teachings of the present invention.

As discussed above, weapon fire simulator 30 is configured to replicate field use automatic weapon fire for various weapons and weapon systems. In the illustrated embodiment simulator 30 is configured to replicate the M16A2. The M16A2 has a maximum firing rate of approximately 600 rounds per minute. Each round fired produces three distinctive shock pulses. The shock pulses along three mutually perpendicular axes can be measured by attaching sensors to the thermal weapon sight while it is attached to an M16A2, during operation.

Pneumatic hammers 36 and 37 are configured to operate at a repetitive rate of 25 to 30 Hz. The repetitive rate of pneumatic hammers 36 and 37 is derived from the equation SR=(FR×P)/60, where: SR is equal to the Shock Rate measured in hertz; FR is equal to the firing rate (e.g. 600 rounds per minute); and P is equal to three pulses per round. The repetitive rate of each pneumatic hammer 36, 37, the cycle time for shock pulses, and the number of cycles per test, may be significantly altered, within the teachings of the present invention, in order to simulate shock pulses corresponding to the particular component of interest.

FIG. 1 illustrates three imaginary, mutually orthogonal axes X, Y, Z. The X axis replicates an axis extending from the front to the rear of thermal weapon site 32. For the purposes of this specification, the front of thermal weapon site 32 represents the end of thermal weapon site 32 having a magnification lens 31. The back of thermal weapon site 32 is the end of having a viewing scope 33. The Y axis extends from side to side with respect to thermal weapon site 32. The Z axis replicates an axis from the top to the bottom of thermal weapon site 32. The bottom of thermal weapon site 32 is the portion of thermal weapon site 32 adjacent to mounting plate 60.

Each pneumatic hammer 36 and 37 is coupled with fixture 58. Pneumatic hammer 36 is an elongate, symmetrical structure whose central axis $C_1$, extends along the plane defined by the X and Z axes. Central axis $C_1$, forms a 45-degree angle with respect to the X axis. Pneumatic hammer 37 is an elongate, symmetrical structure having a longitudinal central axis $C_2$. Central axis $C_2$ extends along the plane defined by the Y and Z axes and forms an angle of approximately 45 degrees with respect to the Y axis.

The configuration of pneumatic hammers 36 and 37, fixture 58 and mounting plate 60 provide a method and system for replicating the shock pulses generated by weapons and weapon systems. It will be recognized by those of ordinary skill in the art that the configuration of weapon fire simulator 30, including the orientation of pneumatic hammers 36 and 37, may be significantly altered, within the teachings of the present invention, in order to simulate field use upon a particular component of interest.

Pneumatic hammer 36 is coupled with an air supply hose 62, which provides pressurized air to pneumatic hammer 36. Similarly, pneumatic hammer 37 is coupled with air supply hose 63, which provides pressurized air to pneumatic hammer 37. Each air supply hose 62 and 63 forms a path of fluid communication between a source of pressured air and pneumatic hammers 36 and 37, respectively. In the illustrated embodiment, air supply hoses 62 and 63 are intended to be coupled with a plant air supply, however, other sources of pressurized air may be used within the teachings of the present invention.

Pneumatic hammers 36 and 37 are coupled with solenoids 122 and 123, respectively, through air supply hoses 62 and 63 which provide power, control and timing of pneumatic hammers 36 and 37. Solenoids 122 and 123 are coupled with programmable logic controller 80 housed in control cabinet 34. Accordingly, control cabinet 34 controls and distributes the flow of air to pneumatic hammers 36 and 37.

In a particular embodiment of the present invention, a removable enclosure 35 may be coupled with weapon fire simulator 30 (FIG. 2). Enclosure 35 provides a barrier between thermal weapon sight 32 and ambient environment. Accordingly, environmental test conditions regarding the particular component being tested may be monitored and/or controlled. Such conditions include, but are not limited to, temperature, pressure and humidity. In a particular embodiment, enclosure 35 may comprise a Styrofoam box coupled with fixture 58.

Control cabinet 34 includes a programmable logic controller 80 which is coupled with switches 88–90 and solenoids 122 and 123. Programmable logic controller 80, in conjunction with regulators 118 and 119, regulates and controls the flow of air to pneumatic hammers 36 and 37. In the illustrated embodiment, programmable logic controller 80 comprises the PLC Direct model DL 105. However, various other programmable logic controllers and their equivalents may be used within the teachings of the present invention.

Programmable logic controller 80 controls the cycle time, time "on", time "off" and the number of cycles each pneumatic hammer 36 and 37 is actuated. In the illustrated embodiment, an electronic timer associated with programmable logic controller 80 limits the amount of run time per cycle to between one second to thirty seconds, during testing.

Programmable logic controller 80 also includes an operator interface 84 having an LCD display which indicates the current number of cycles that are running and/or the amount of cycles that have run. Operator interface 84 also includes a programmable panel which allows the operator to change the number of cycles, and/or the time in which a particular pneumatic hammer actuates on, or off.

A pair of pressure gauges 86 and 87 and pressure regulators 118 and 119, associated with programmable logic controller 80, allow the operator to adjust the pressure of pressurized air provided to pneumatic hammers 36 and 37, respectively. In the illustrated embodiment, pressure gauges 86 and 87 may be adjusted between 0 and 200 pounds per square inch (psi). Accordingly, the magnitude of the shock pulses provided by pneumatic hammers 36 and 37 may be independently adjusted allowing the operator to achieve the desired shock pulses along three mutually perpendicular axis. In a particular embodiment of the present invention, pressure gauges 86 and 87 are set to provide pressurized air at a pressure of approximately 30 pounds per square inch, to pneumatic hammers 36 and 37.

Switches 88–90 are provided to control the operation of weapon fire simulator 30. Switch 88 is a "start" button which actuates weapon fire simulator 30. Switch 89 is a "stop" button which allows the operator to discontinue operation at any point in time. Reset switch 90 resets a counter associated with operator interface 84 back to zero, indicating that a new cycle or cycles are beginning. Reset switch 90 allows the operator to track the number of cycles which have already run, at operator interface 84.

A multi-channel accelerometer amplifier 82, in conjunction with accelerometers 92–94 are used to monitor the shock amplitude and repetitive rate of weapon fire simulator 30. Accelerometer amplifier 82 is coupled with accelerometers 92–94 located in this particular embodiment on the thermal weapon site 32. Each accelerometer 92–94 is electrically coupled with control wires 64. Data collected by accelerometer amplifier 82 from accelerometers 92–94 are analyzed in the frequency domain using a Spectral Dynamics vibration controller/analyzer 96 which comprises monitor 98, keyboard 100, mouse 101, VCS box 102, Sun Workstation 104 and printer 106. The Vibration Controller converts the real time wave forms to shock response spectra (SRS) SRS is a calculation of the response of a system to a particular shock pulse or pulses. This allows the operator to determine the actual shock pulses experienced by thermal weapon site 32 during operation.

Such data may be used and compared to actual data collected during field use in order to determine the effectiveness of the simulation. The resulting SRS wave forms may then be compared to actual field data, and pressure regulators 118 and 119 may be adjusted to more accurately reflect the actual field data, and optimize the simulator output.

Figure 6:
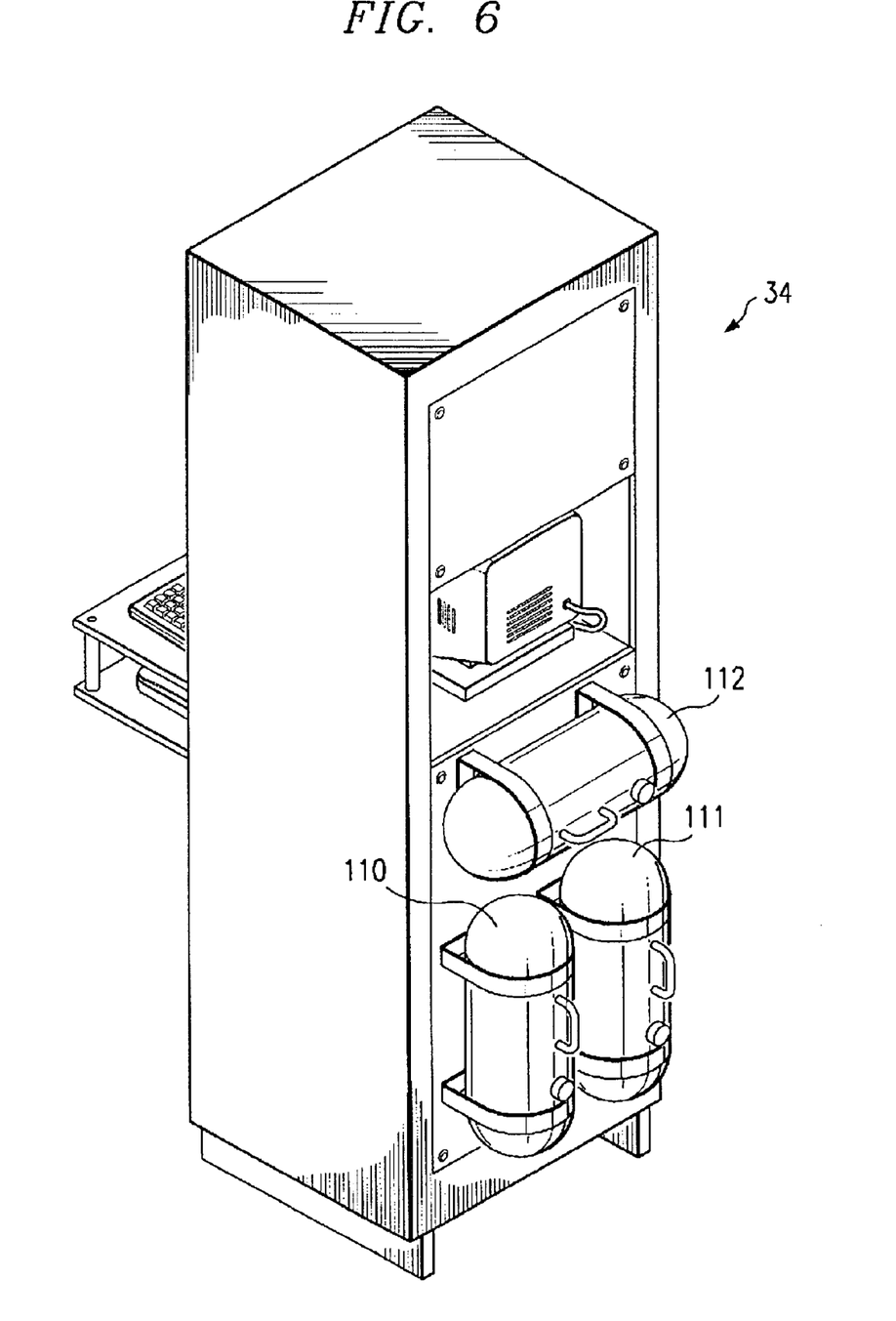
FIG. 6 is an isometric, rear view of a control cabinet of the system of FIG. 1, in accordance with a particular embodiment of the present invention.

FIG. 6 illustrates a rear view of control cabinet 34. Three accumulator tanks 110–112 are coupled with control cabinet 34. Tanks 110–112 provide storage for pressurized air to ensure that sufficient volume and/or airflow is available to pneumatic hammers 36 and 37. In the illustrated embodiment, accumulator tanks 110–112 each comprise 85 cubic inch accumulators. Accumulator tanks 110–112 will be discussed in more detail with regard to FIG. 7.

Figure 7:
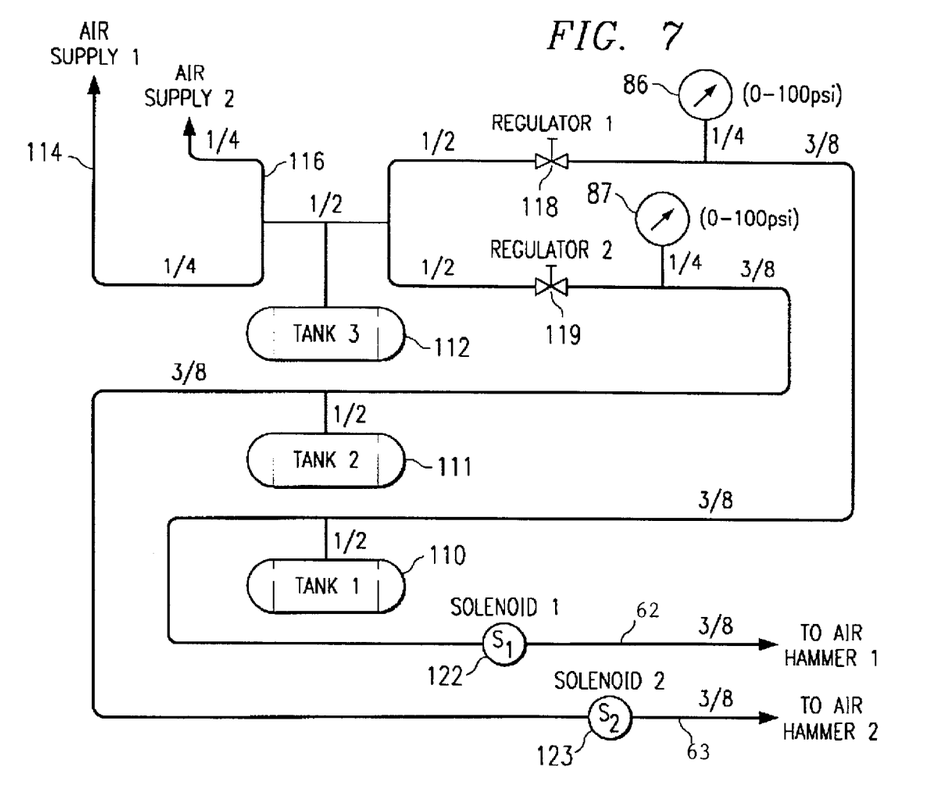
FIG. 7 is a piping and instrumentation diagram regarding the system of FIG. 1, in accordance with a particular embodiment of the present invention.

FIG. 7 illustrates a piping and instrumentation diagram regarding weapon fire simulator 30. Two air supply hoses 114 and 116 are coupled with accumulator tank 112. Accumulator tank 112 collects pressurized air for distribution to regulators 118 and 119. Regulators 118 and 119 regulate the flow of pressurized air to pneumatic hammers 36 and 37, respectively. Pressure gauges 86 and 87 are coupled with regulators 118 and 119, respectively, and together provide a user interface to control and view the pressures of pressurized air being introduced to pneumatic hammers 36 and 37. Accumulator tank 110 is coupled with regulator 118, and accumulates pressured air for distribution to pneumatic hammer 36. Similarly, accumulator tank 111 is coupled with regulator 119 and accumulates pressured air for distribution to pneumatic hammer 37.

Pressurized air enters pneumatic hammers 36 and 37 through supply hoses 62 and 63, respectively. Solenoid valve 122 controls the flow of pressurized air though air supply hose 62 to pneumatic hammer 36. When solenoid valve 122 air is "open", pressurized air enters pneumatic hammer 36 and shock pulses are generated by the operation of pneumatic hammer 36.

Similarly, solenoid valve 123 controls the flow of pressurized air through air supply hose 63 to pneumatic hammer 37. When solenoid valve 123 is "open", pressurized air is provided to pneumatic hammer 37 and shock pulses are generated by the operation of pneumatic hammer 37. Each regulator 118 and 119, and solenoid valve 122 and 123 may be independently controlled by programmable logic controller 80. Therefore, programmable logic controller 80 may be programmed to provide pressurized air to pneumatic hammers 36 and 37 for predetermined time intervals, at predetermined pressures and/or for a predetermined number of cycles.

In the illustrated embodiment, air supply hoses 114 and 115 comprise ⅜" air hoses. Accumulator tanks 110–112 are used to ensure that an adequate volume of pressurized air is available to pneumatic hammers 36 and 37. In alternative embodiments where the supply of pressurized air is adequate, fewer than three accumulator tanks may be utilized within the teachings of the present invention. In fact, if the appropriate pressurized air source is used, accumulator tanks may be completely eliminated from the system.

Figure 8:
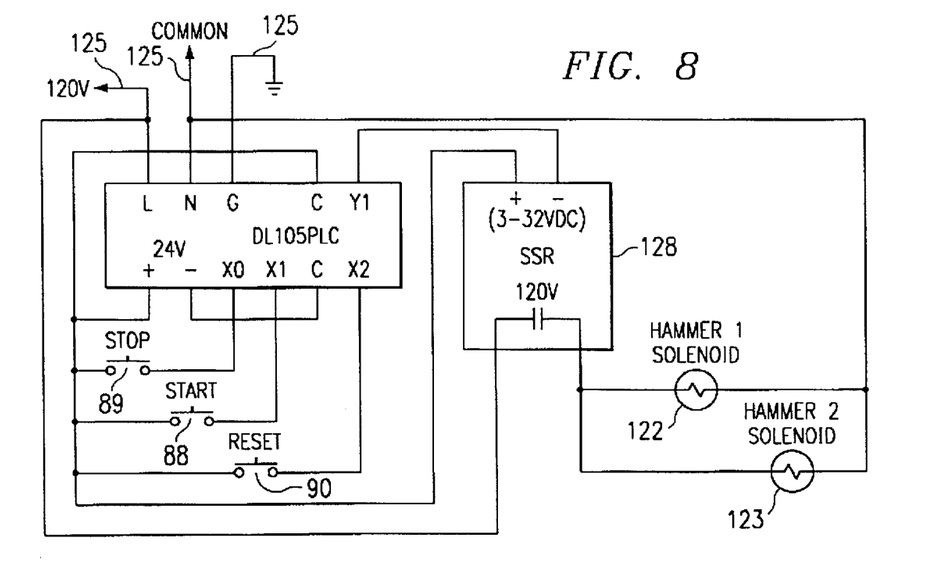
FIG. 8 is a wiring diagram regarding the system of FIG. 1, in accordance with a particular embodiment of the present invention.

FIG. 8 illustrates a wiring diagram regarding weapon fire simulator 30. 120 volt power is provided to programmable logic controller 80 through a plurality of wires 125. The operation of programmable logic controller 80 is controlled by switches 88–90, as previously described. Each solenoid valve 122 and 123 is coupled with solid state relay (SSR) 128. Solid state relay 128 controls the operation of solenoid valves 122 and 123. In the illustrated embodiment, solid state relay 128 uses 24-volt power internally generated by programmable logic controller 80. Programmable logic control 80 uses 24-volt control wiring. Each solenoid valve 122 and 123 uses 115 volt power. Accordingly, an interface is used between programmable logic controller 80 and solenoid valves 122 and 123. Solid state relay 128 provides this interface.

In accordance with a particular embodiment, the teachings of the present invention provide a system and method to simulate and analyze weapon shock impact of a component of a weapon or weapon system, for example a thermal sight. Components suitable for testing include the W1000, Thermal Weapon Sight (TWS), LTWS, and TIPS, all of which are manufactured by Raytheon. However, weapon fire simulator 30 may be used on various components associated with weapons and weapon systems of all manufacturers.

Furthermore, the teachings of the present invention may be used to test subsystems of weapons and weapon systems. For example, mounting plate 60 may be configured to receive components of thermal weapon sight 32. Such components include, but are not limited to thermal detectors, thermal coolers and other elements and components associated with weapon system components. In fact, the teachings of the present invention provide a system and method for testing, analyzing, screening for compliance to specification, and/or evaluating practically any component which is subject to, and sensitive of shock pulses experienced during operation. In particular embodiments, such components include practically anything mounted on or near an automatic weapon.

Although the present invention has been described in several embodiments, a myriad of changes and modifications will be apparent to one skilled in the art, and it is intended that the present invention encompass such changes and modifications as fall within the scope of the present appended claims.

What is claimed is:

1. A system, comprising:
a fixture having first and second faces;
a mounting plate coupled with the first face;
the mounting plate being adapted to receive a component for testing of the component;
first and second pneumatic hammers coupled with the second face, the first and second pneumatic hammers being operable to subject the mounting plate to simulated shock pulses;
at least one accelerometer for coupling with the component, the accelerometer being operable to measure a magnitude of shock pulses generated by the first and second pneumatic hammers; and
a programmable logic controller being operable to control pressurized air flows to first and second hoses that supply the pressurized air to the first and second pneumatic hammers, respectively, based, at least in part, upon the shock pulses measured by the at least one accelerometer.

2. The system of claim 1, wherein the simulated shock pulses approximately simulate actual shock pulses to be experienced by the component while the component is coupled with, and during operation of, an automatic weapon.

3. The system of claim 2, wherein the component comprises a weapon sight adapted to be coupled with the automatic weapon.

4. The system of claim 2, wherein the component comprises an element of a weapon sight.

5. The system of claim 1, wherein the component comprises a weapon sight adapted to be coupled with an automatic weapon, and wherein the actual shock pulses approximately simulate automatic weapon shock pulses to be experienced by the weapon sight along three mutually perpendicular axes, while the weapon sight is coupled with, and during operation of, an automatic weapon.

6. The system of claim 1, further comprising an enclosure coupled with the fixture, the enclosure being operable to provide a controllable environment for testing.

7. The system of claim 1, further comprising a pressure regulator coupled with the first pneumatic hammer, the pressure regulator being operable to regulate the flow of pressurized air to the first pneumatic hammer.

8. A method for testing a component, comprising:
coupling the component with a fixture, the fixture having first and second pneumatic hammers coupled therewith;
providing flows of pressurized air to the first and second pneumatic hammers;
measuring shock pulses the component is subjected to by the first and second pneumatic hammers, using at least one accelerometer;
controlling, based at least in part upon the shock pulses measured by the accelerometer, the flows of pressurized air to the first and second pneumatic hammers, respectively, using a programmable logic controller; and
wherein the pneumatic hammers are operable to subject the component to the shock pulses, in response to receiving the flows of pressurized air.

9. The method of claim 8, wherein the component comprises a weapon sight adapted to be coupled with an automatic weapon.

10. The method of claim 8, wherein the component comprises an element of a weapon sight.

11. The method of claim 8, further comprising coupling pressure regulators with the first and second pneumatic hammers, respectively, the pressure regulators being operable to regulate the flows of pressurized air to the first and second pneumatic hammers.

12. The method of claim 8, further comprising coupling an enclosure with the fixture, the enclosure being operable to provide a controllable environment for testing of the component.

13. The method of claim 12, further comprising controlling environmental conditions exposed to the component.

14. The method of claim 8, further comprising approximately simulating automatic weapon shock pulses to be experienced by the component while the component is coupled with, and during operation of, an automatic weapon, using the simulated shock pulses measured by the accelerometers.

15. The method of claim 9, further comprising approximately simulating automatic weapon shock pulses to be experienced by the weapon sight along three mutually perpendicular axes while the weapon sight is coupled with the automatic weapon.

16. A system, comprising:

a fixture having first and second faces;

a mounting plate coupled with the first face;

the mounting plate being adapted to receive a component for testing of the component;

first and second pneumatic hammers coupled with the second face, the first and second pneumatic hammers being operable to subject the mounting plate to simulated shock pulses;

a programmable logic controller being operable to control pressurized air flows to first and second hoses that supply the pressurized air to the first and second pneumatic hammers, respectively, a plurality of accelerometers coupled with the component, each accelerometer being electrically coupled with an accelerometer amplifier; and the accelerometer amplifier being operable to determine the magnitude of shock pulses being generated by the first and second pneumatic hammers.

17. A method for testing a component, comprising:

coupling the component with a fixture, the fixture having first and second pneumatic hammers coupled therewith;

providing flows of pressurized air to the first and second pneumatic hammers;

controlling the flows of pressurized air to the first and second pneumatic hammers, respectively, using a programmable logic controller;

wherein the pneumatic hammers are operable to subject the component to simulated shock pulses, in response to receiving the flows of pressurized air;

coupling a plurality of accelerometers with the component; and each accelerometer being adapted to be electrically coupled with an accelerometer amplifier.

18. A method for testing a component, comprising:

coupling the component with a fixture, the fixture having first and second pneumatic hammers coupled therewith;

providing flows of pressurized air to the first and second pneumatic hammers;

controlling the flows of pressurized air to the first and second pneumatic hammers, respectively, using a programmable logic controller;

wherein the pneumatic hammers are operable to subject the component to simulated shock pulses, in response to receiving the flows of pressurized air; and measuring the magnitude of shock pulses exerted by the first and second pneumatic hammers, using the accelerometers.

19. A system for simulating shock pulses generated by an automatic weapon during operation thereof, comprising:

means for coupling a component with a fixture;

means for subjecting the component to at least two simulated shock pulses simultaneously;

means for measuring actual shock pulses experienced by the component; and means for controlling, based at least in part upon the actual shock pulses, the at least two simulated shock pulses such that the actual shock pulses approximately simulate automatic weapon shock pulses to be experienced by the component while the component is coupled with, and during operation of an automatic weapon.

* * * * *

UNITED STATES PATENT AND TRADEMARK OFFICE
CERTIFICATE OF CORRECTION

PATENT NO. : 6,634,209 B1
DATED : October 21, 2003
INVENTOR(S) : William A. Kastendieck et al.

It is certified that error appears in the above-identified patent and that said Letters Patent is hereby corrected as shown below:

Column 6,
Line 14, change "(SRS) SRS is a" to -- (SRS). SRS is a --;
Line 50, change "though" to -- through --

Column 8,
Line 67, delete "simulated".

Signed and Sealed this

Tenth Day of August, 2004

JON W. DUDAS
*Acting Director of the United States Patent and Trademark Office*